(12) United States Patent
Zeuthen et al.

(10) Patent No.: US 10,914,728 B2
(45) Date of Patent: Feb. 9, 2021

(54) BIOASSAY FOR INSULIN FORMULATIONS

(71) Applicant: Novo Nordisk A/S, Bagsvaerd (DK)

(72) Inventors: Louise Hjerrild Zeuthen, Birkeroed (DK); Jan Amstrup, Greve (DK); Thomas Aaskov Pedersen, Ringsted (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/335,060

(22) PCT Filed: Oct. 24, 2017

(86) PCT No.: PCT/EP2017/077120
§ 371 (c)(1),
(2) Date: Mar. 20, 2019

(87) PCT Pub. No.: WO2018/077851
PCT Pub. Date: May 3, 2018

(65) Prior Publication Data
US 2019/0361007 A1 Nov. 28, 2019

(30) Foreign Application Priority Data
Oct. 24, 2016 (EP) .................................... 16195387

(51) Int. Cl.
*G01N 33/50* (2006.01)
*A61K 38/28* (2006.01)

(52) U.S. Cl.
CPC ......... *G01N 33/5041* (2013.01); *A61K 38/28* (2013.01); *G01N 2333/62* (2013.01)

(58) Field of Classification Search
CPC .. A61K 38/28; G01N 2333/62; G01N 33/502; G01N 33/5041
See application file for complete search history.

(56) References Cited

U.S. PATENT DOCUMENTS

| | | | |
|---|---|---|---|
| 7,220,539 B1 | 5/2007 | Du et al. | |
| 2005/0014682 A1 | 1/2005 | Mueckler et al. | |
| 2006/0160076 A1 | 7/2006 | Moodie et al. | |
| 2011/0076284 A1 | 3/2011 | Corbin et al. | |
| 2012/0100071 A1 | 4/2012 | Valliant et al. | |
| 2015/0320837 A1 | 11/2015 | Anderson et al. | |

FOREIGN PATENT DOCUMENTS

| | | |
|---|---|---|
| WO | 9722360 A2 | 6/1997 |
| WO | 0175142 A2 | 10/2001 |
| WO | 03087761 A2 | 10/2003 |
| WO | 2005054257 A1 | 6/2005 |
| WO | 2016081670 A2 | 5/2016 |

OTHER PUBLICATIONS

Kim et al. Divergent Regulation of Akt1 and Akt2 Isoforms in Insulin Target Tissues of Obese Zucker Rats. Diabetes, vol. 49, May 2000. pp. 847-856. (Year: 2000).*
Corbin et al. Improved Glucose Metabolism In Vitro and In Vivo by an Allosteric Monoclonal Antibody That Increases Insulin Receptor Binding Affinity. Plos One, Feb. 2014, vol. 9, No. 2, e88684, pp. 1-12. (Year: 2014).*
Baricevic et al., "A Framework for the In Vitro Evaluation of Cancer-Relevant Molecular Characteristics and Mitogenic Potency of Insulin Analogues," Carcinogenesis, 2015, vol. 36, No. 9, pp. 1040-1050.
Bertacca et al., "Continually High Insulin Levels Impair Akt Phosphorylation and Glucose Transport in Human Myoblasts," Metabolism, Clinical and Experimental, 2005, vol. 54, No. 12, pp. 1687-1693.
Eckardt et al., "IGF-1 Receptor Signalling Determines the Mitogenic Potency of Insulin Analogues in Human Smooth Muscle Cells and Fibroblasts," Diabetoligia; Clinical and Experimental Diabetes and Metabolism, 2007, vol. 50, No. 12, pp. 2534-2543.
Tan et al., "Amplification and Demultiplexing in Insulin-Regulated Akt Protein Kinase Pathway in Adipocytes," J Biol Chem., 2012, vol. 287, No. 9, pp. 6128-6138.

* cited by examiner

*Primary Examiner* — Marcela M Cordero Garcia
(74) *Attorney, Agent, or Firm* — Jianjie Hu

(57) ABSTRACT

The invention relates to a bioassay of insulin peptide in oral formulations and low affinity insulin peptides in liquid formulations, by for quantifying phosphorylated Akt, thereby avoiding the interference of excipients in potency determination.

11 Claims, 8 Drawing Sheets

Specification includes a Sequence Listing.

BIOASSAY FOR INSULIN FORMULATIONS

CROSS-REFERENCE TO RELATED APPLICATIONS

This application is a 35 U.S.C. § 371 National Stage application of International Application PCT/EP2017/077120 (WO 2018/077851), filed Oct. 24, 2017, which claims priority to European Patent Application 16195387.2, filed Oct. 24, 2016; the contents of which are incorporated herein by reference.

In accordance with 37 C.F.R. § 1.52(e)(5), Applicants enclose herewith the Sequence Listing for the above-captioned application entitled "160020US01_SeqList.txt", created on Mar. 14, 2018. The Sequence Listing is made up of 7 kilobytes, and the information contained in the attached "SEQUENCE LISTING" is identical to the information in the specification as originally filed. No new matter is added.

TECHNICAL FIELD

The present invention relates to a bioassay for insulin peptide in oral formulations and low affinity insulin peptide in liquid formulations.

BACKGROUND OF THE INVENTION

Bioassays are biological assays (in vivo assays, ex vivo assays, cell based in vitro assays, binding assays, biochemical assays etc.) are used for various purposes such as process development, process characterization, and product development; product release testing for drug substance or drug product; in-process control and intermediates testing; stability and product integrity testing etc. Bioassays are also used as qualitative test, i.e. potency or bioidentity tests. Bioassays are susceptible to many variables, so activity may vary between assays. Absolute measure of potency is more variable than measure of activity relative to a standard. Therefore, relative potency method is used where the activity of a component is measured relative to a designated standard/reference made up of similar material.

Potency is a measure of drug activity expressed in terms of the amount required to produce an effect of given intensity. A highly potent drug evokes a given response at low concentrations, while a drug of lower potency evokes the same response only at higher concentrations. The potency depends on both the affinity and efficacy of the drug. Affinity is the ability of the drug to bind to a receptor. Efficacy is the relationship between receptor occupancy and the ability to initiate a response at the molecular level.

The determination of potency is often influenced by matrix meaning that the excipients of the formulations can interfere with the performance of the bioassay. This is often referred to as "matrix effect". This represents a technical problem, as the matrix effects of the excipients prevent testing the potency of the drug in conventional assays. Insulin in oral formulation and low affinity insulin in liquid formulation are challenging to bioassay as the excipients of these formulations interfere with the performance of the assay and prevents potency determination by conventional assays such as Insulin receptor phosphorylation assay and Reporter gene assay.

It is an object of this invention to overcome or ameliorate at least one of the disadvantages of the prior art, or to provide a useful alternative.

SUMMARY

The present invention relates to a bioassay of insulin peptide in oral formulations and low affinity insulin peptide in liquid formulations.

In one aspect the present invention relates to a method for measuring the potency of a drug product relative to the drug substance, wherein the method comprises the step of quantifying phosphorylated Akt, wherein the drug product is an insulin peptide in an oral formulation or is a low affinity insulin peptide in a liquid formulation.

The present invention may also solve further problems that will be apparent from the disclosure of the exemplary embodiments.

DESCRIPTION

Figure 1:
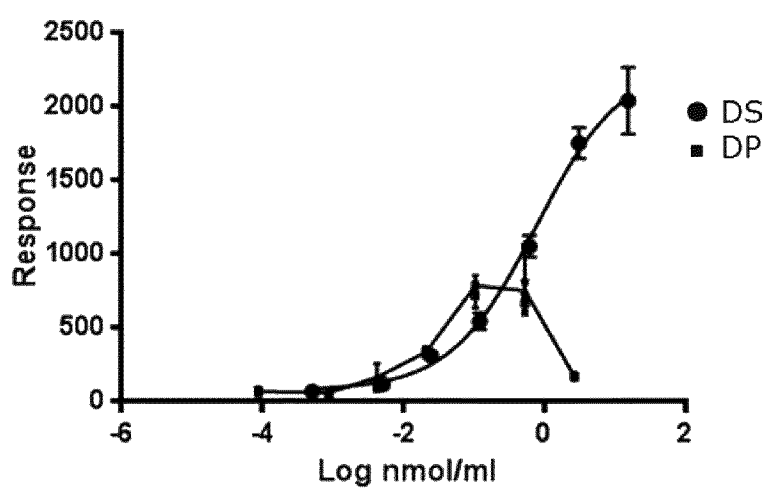
FIG. 1: InsR phosphorylation assay for A14E, B25H, B29K($N^\epsilon$Octadecanedioyl-gGlu-OEG-OEG), desB30 human insulin in oral formulation.

The present invention relates to a bioassay of insulin peptide in oral formulation and low affinity insulin peptide in liquid formulation.

It has surprisingly been found that phosphorylated Akt (pAkt) bioassays overcome the problem of interference by excipients encountered by traditional bioassays and allows potency determination of insulin peptide in oral formulations or low affinity insulin peptide in liquid formulations.

The present invention relates to a method for measuring the potency of a drug product relative to the drug substance, wherein the method comprises the step of quantifying phosphorylated Akt, wherein the drug product is an insulin peptide in an oral formulation or is a low affinity insulin peptide in a liquid formulation.

The present invention relates to a method for measuring the potency of an insulin peptide. The utility of the present invention is that it avoids interference of excipients in oral formulation comprising insulin peptide or liquid formulation comprising low affinity insulin peptide.

Unless otherwise indicated in the specification, terms presented in singular form also include the plural situation.

Terms such as bioassay, biological assay, biological assessment, biological standardization, bio-identity or potency are used interchangeably.

The present invention may also solve further problems that will be apparent from the disclosure of the exemplary embodiments.

Drug Product

The term "Drug product" (DP) as used herein means the Active Pharmaceutical Ingredient (API) exerting the pharmacological action with excipients included in the formulation.

Drug Substance

The term "Drug Substance" (DS) as used herein means the Active Pharmaceutical Ingredient (API) exerting the pharmacological action.

Insulin

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

"An insulin" as used herein is to be understood as human insulin or an insulin from another species such as porcine or bovine insulin.

The term "parent insulin" as used herein is intended to mean an insulin before any modifications according to the present invention have been applied thereto.

Insulin Peptide

The term "insulin peptide" as used herein means a peptide which is either human insulin or an analogue or a derivative thereof with insulin activity.

Insulin Analogue

The term "insulin analogue" as used herein means a modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin.

In one embodiment an insulin analogue comprises less than 10 amino acid modifications (substitutions, deletions, additions (including insertions) and any combination thereof) relative to human insulin, alternatively less than 9, 8, 7, 6, 5, 4, 3, 2 or 1 modification relative to human insulin.

Modifications in the insulin molecule are denoted stating the chain (A or B), the position, and the one or three letter code for the amino acid residue substituting the native amino acid residue.

By "connecting peptide" or "C-peptide" is meant a connection moiety "C" of the B-C-A polypeptide sequence of a single chain proinsulin-molecule. In the human insulin chain, the C-peptide connects position 30 of the B chain and position 1 of the A chain and is 35 amino acid residue long. The connecting peptide includes two terminal dibasic amino acid sequence, e.g., Arg-Arg and Lys-Arg which serve as cleavage sites for cleavage off of the connecting peptide from the A and B chains to form the two-chain insulin molecule.

By "desB30" or "B(1-29)" is meant a natural insulin B chain or an analogue thereof lacking the B30 amino acid and "A(1-21)" means the natural insulin A chain. Thus, e.g., A21Gly, B28Asp, desB30 human insulin is an analogue of human insulin where the amino acid in position 21 in the A chain is substituted with glycine, the amino acid in position 28 in the B chain is substituted with aspartic acid, and the amino acid in position 30 in the B chain is deleted.

Herein terms like "A1", "A2" and "A3" etc. indicates the amino acid in position 1, 2 and 3 etc., respectively, in the A chain of insulin (counted from the N terminal end). Similarly, terms like B1, B2 and B3 etc. indicates the amino acid in position 1, 2 and 3 etc., respectively, in the B chain of insulin (counted from the N terminal end). Using the one letter codes for amino acids, terms like A21A, A21G and A21C designates that the amino acid in the A21 position is A, G and Q, respectively. Using the three letter codes for amino acids, the corresponding expressions are A21Ala, A21Gly and A21Gln, respectively.

Herein the terms "A(0)" or "B(0)" indicate the positions of the amino acids N-terminally to A1 or B1, respectively. The terms A(−1) or B(−1) indicate the positions of the first amino acids N-terminally to A(0) or B(0), respectively. Thus A(−2) and B(−2) indicate positions of the amino acids N-terminally to A(−1) and B(−1), respectively, A(−3) and B(−3) indicate positions of the amino acids N-terminally to A(−2) and B(−2), respectively, and so forth. The terms A22 or B31 indicate the positions of the amino acids C-terminally to A21 or B30, respectively. The terms A23 or B32 indicate the positions of the first amino acids C-terminally to A22 or B31, respectively. Thus A24 and B33 indicate positions of the amino acids C terminally to A23 and B32, respectively, and so forth.

Herein, the term "amino acid residue" is an amino acid from which, formally, a hydroxy group has been removed from a carboxy group and/or from which, formally, a hydrogen atom has been removed from an amino group.

Examples of insulin analogues are such wherein Pro in position 28 of the B chain is substituted with Asp, Lys, Leu, Val, or Ala and/or Lys at position B29 is substituted with Pro, Glu or Asp. Furthermore, Asn at position B3 may be substituted with Thr, Lys, Gln, Glu or Asp. The amino acid residue in position A21 may be substituted with Gly. Also one or more amino acids may be added to the C-terminal of the A-chain and/or B-chain such as, e.g., Lys. The amino acid in position B1 may be substituted with Glu. The amino acid in position B16 may be substituted with Glu or His. Further examples of insulin analogues are the deletion analogues, e.g., analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues.

Further examples of insulin analogues include: DesB30 human insulin; AspB28 human insulin; AspB28, desB30 human insulin; LysB3,GluB29 human insulin; LysB28, ProB29 human insulin; GlyA21,ArgB31,ArgB32 human insulin; GluA14,HisB25 human insulin; HisA14,HisB25 human insulin; GluA14,HisB25,desB30 human insulin; HisA14, HisB25,desB30 human insulin; GluA14,HisB25, desB27,desB28,desB29,desB30 human insulin; GluA14, HisB25,GluB27,desB30 human insulin; GluA14,HisB16, HisB25,desB30 human insulin; HisA14,HisB16,HisB25, desB30 human insulin; HisA8,GluA14,HisB25,GluB27, desB30 human insulin; HisA8,GluA14,GluB1,GluB16, HisB25,GluB27,desB30 human insulin; and HisA8, GluA14,GluB16,HisB25,desB30 human insulin.

Insulin Derivative

The term "insulin derivative" as used herein means chemically modified parent insulin or an analogue thereof, wherein the modification(s) are in the form of attachment of amides, carbohydrates, alkyl groups, acyl groups, esters, PEGylations, and the like. Examples of derivatives of human insulin according to the invention are human insulin B30 threonine methyl ester, GlyA21,ArgB31,Arg-amideB32 human insulin, $N^\varepsilon$B29-tetradecanoyl desB30 human insulin, $N^\varepsilon$B29-tetradecanoyl human insulin, $N^\varepsilon$B29-decanoyl desB30 human insulin, $N^\varepsilon$B29-dodecanoyl desB30 human insulin, $N^\varepsilon$B29-3-(2-{2-(2-methoxyethoxy)-ethoxy}-ethoxy)-propionyl human insulin, LysB29($N^\varepsilon$-hexadecandioyl-γ-Glu) des(B30) human insulin); $N^\varepsilon$B29-($N^\alpha$-(Sar-OC(CH2)13CO)-γ-Glu) desB30 human insulin, $N^\varepsilon$B29-carboxy-pentadecanoyl-L-glutamylamide desB30 human insulin, $N^\varepsilon$B29-hexadecandioyl-amino-butanoyl desB30 human insulin, $N^\varepsilon$B29-hexadecandioyl-L-Glu-amide desB30 insulin, A14E, B16E, B25H, B29K(N(eps) eicosanedioyl-gGlu-2×OEG), desB30 human insulin (SEQ ID NO. 1 and SEQ ID NO. 2), A14E, B16H, B25H, B29K(N(eps)Eicosanedioyl-γGlu-OEG-OEG), desB30 human insulin (SEQ ID NO. 3 and SEQ ID NO. 4), A14E, B25H, desB27, B29K($N^\varepsilon$Octadecanedioyl-γGlu-OEG-OEG), desB30 human insulin (SEQ ID NO. 5 and SEQ ID NO. 6); A14E, B16H, B25H, B29K($N^\varepsilon$Eicosanedioyl-γGlu), desB30 human insulin (SEQ ID NO. 7 and SEQ ID NO. 8); A14E, B25H, B29K($N^\varepsilon$Octadecanedioyl-gGlu-OEG-OEG), desB30 human insulin (SEQ ID NO. 9 and SEQ ID NO. 10); A14E, B25H, desB27, B29K($N^\varepsilon$-(octadecandioyl-gGlu), desB30 human insulin (SEQ ID NO. 11 and SEQ ID NO. 12).

The term "PEGylated insulin/insulin analogue/insulin derivative" means a PEG molecule conjugated to a insulin/insulin analogue/insulin derivative. It is to be understood, that the PEG molecule may be attached to any part of the insulin/insulin analogue/insulin derivative polypeptide including any amino acid residue or carbohydrate moiety of the insulin/insulin analogue/insulin derivative.

The term "cysteine-PEGylated insulin/insulin analogue/insulin derivative" means "an insulin/insulin analogue/insulin derivative" having a PEG molecule conjugated to a sulfhydryl group of a cysteine introduced in "an insulin/insulin analogue/insulin derivative".

The term "polyethylene glycol" or "PEG" means a polyethylene glycol compound or a derivative thereof, with or without coupling agents, coupling or activating moeities (e.g., with thiol, triflate, tresylate, azirdine, oxirane, or preferably with a maleimide moiety). Compounds such as maleimido monomethoxy PEG are exemplary of activated PEG compounds of the invention.

PEG is a suitable polymer molecule, since it has only few reactive groups capable of cross-linking compared to polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule are provided in activated form, i.e. with reactive functional groups. Suitable activated polymer molecules are commercially available, e.g. from Shearwater Corp., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Corp. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575.

The conjugation of the polypeptide and the activated polymer molecules is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al. (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfhydryl, succinimidyl, maleimide, vinylsulfone or haloacetate).

Low Affinity Insulin

Low affinity insulin according to the invention means Insulin analogues and insulin derivatives with low relative potency i.e. <0.08% of that of Human Insulin when measured according to pAkt assay.

Pharmaceutical Formulations

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in of such a treatment.

The pharmaceutical compositions may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

In one embodiment of the invention the pharmaceutical formulation is a liquid formulation. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution.

The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In one embodiment of the invention the pharmaceutical formulation is an oral formulation. In one embodiment the formulation comprises granules which have been manufactured by dry granulation. In one embodiment the formulation comprises granules which have been manufactured by roller compaction. In one embodiment the moldings from the roller compaction process are comminuted into granules. In one embodiment the term "granulate" refers to one or more granules. In one embodiment the term "granule" refers to particles gathered into larger particles.

In some embodiments the granule comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101.

In some embodiments the granule comprises a binder, such as 35 lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, Lhydroxypropylcellulose (low-substituted), hypromellose (HPMC) (e.g. Methocel E, F and K, Metolose SH of Shin-Etsu, Ltd, such as, e.g., the 4,000 cps grades of Methocel E and 5 Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, 10 starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as povidone K 90.

In some embodiments the granule comprises a disintegrant, such as alginic acid, alginates, microcrystalline cellulose, hydroxypropyl cellulose, other cellulose derivatives, croscarmellose sodium, crospovidone, polacrillin potassium, sodium starch glycolate, starch, pregelatinized starch, or carboxymethyl starch (e.g. Primogel® and Explotab®).

In some embodiments the granule comprises a lubricant, such as stearic acid, magnesium stearate, calcium stearate or other metallic stearate, talc, waxes, glycerides, light mineral oil, glyceryl behenate, hydrogenated vegetable oils, sodium stearyl fumarate, polyethylene glycols, alkyl sulfates, or sodium benzoate. In some embodiments the COMPOSITION or granule comprises a lubricant, such as magnesium silicate, talc, or colloidal silica. In some embodiments the lubricant is magnesium stearate.

In some embodiments the comprises one or more excipients selected from crystallization retarders, such as Povidone, etc.; solubilizing agents (also known as surfactants), such as anionic surfactants (e.g. Pluronic or Povidone), cationic surfactants, nonionic surfactants, and/or zwitterionic surfactants; colouring agents, including dyes and pigments, such as Iron Oxide Red or Yellow, titanium dioxide, and/or talc; and/or pH control agents, such as citric acid, tartaric acid, fumaric acid, sodium citrate, dibasic calcium phosphate, and/or dibasic sodium phosphate.

In one embodiment the formulation is in the form of a solid dosage form. In one embodiment the formulation is in the form of a tablet. In one embodiment of the invention oral formulation means a formulation wherein drug product is present as 800-10800 nmol/tablet. In one embodiment the formulation is in the form of a capsule. In one embodiment the formulation is in the form of a sachet.

In another embodiment the pharmaceutical formulation is a dried formulation (e.g. freeze-dried or spray-dried) ready for use without any prior dissolution.

The formulation may comprise at least one pharmaceutically acceptable excipient. The term "excipient" as used herein broadly refers to any component other than the active pharmaceutical ingredient. The excipient may be an inert substance, which is inert in the sense that it substantially does not have any therapeutic and/or prophylactic effect per se. The excipient may serve various purposes, e.g. as a delivery agent, absorption enhancer, vehicle, filler (also known as diluents), binder, lubricant, glidant, disintegrant, crystallization retarders, acidifying agent, alkalizing agent, preservative, antioxidant, buffer or buffering agent, isotonic agent, chelating agent, complexing agents, surfactant agent, emulsifying and/or solubilizing agents, sweetening agents, wetting agents, stabilizer or stabilizing agent, colouring agent, flavouring agent, and/or to improve administration, and/or absorption of the active substance. A person skilled in the art may select one or more of the aforementioned excipients with respect to the particular desired properties of the pharmaceutical formulation by routine experimentation and without any undue burden. The amount of each excipient used may vary within ranges conventional in the art.

Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In a further embodiment of the invention the formulation further comprises a pharmaceutically acceptable buffer. The buffer may be selected from the group consisting of acetate, carbonate, citrate, glycylglycine, histidine, glycine, phosphate, hydrogen phosphate, and tris(hydroxymethyl)-aminomethan (TRIS), bicine, tricine, succinate, aspartic acid, asparagine or mixtures thereof.

In a further embodiment of the invention the formulation further comprises a pharmaceutically acceptable preservative. In a further embodiment of the invention the preservative is selected from the group consisting of phenol, m-cresol, methyl p-hydroxybenzoate, propyl p-hydroxybenzoate, 2-phenoxyethanol, butyl p-hydroxybenzoate, benzyl alcohol, chlorobutanol, benzoic acid, imidurea, chlorocresol, ethyl p-hydroxybenzoate, benzethonium chloride1, or mixtures thereof. The use of a preservative in pharmaceutical compositions is well-known to the skilled person. For convenience reference is made to Remington: The Science and Practice of Pharmacy, 19th edition, 1995.

In a further embodiment of the invention the formulation further comprises an isotonic agent. The isotonic agent may be selected from the group consisting of a salt (e.g. sodium chloride), a sugar such as mono-, di-, or polysaccharides, or water-soluble glucans, including for example fructose, glucose, mannose, lactose, sucrose, trehalose, dextran, or sugar alcohol such as, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Sugar alcohol includes, for example, mannitol, sorbitol, inositol, galactitol, dulcitol, xylitol, and arabitol.

The use of an isotonic agent in pharmaceutical compositions is well-known to the skilled person. For convenience reference is made to Remington: The Science and Practice of Pharmacy, 19th edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, EGTA, and mixtures thereof.

In a further embodiment of the invention the formulation further comprises a stabilizer. The use of a stabilizer in pharmaceutical compositions is well-known to the skilled person. For convenience reference is made to Remington: The Science and Practice of Pharmacy, 19th edition, 1995.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

The pharmaceutical compositions of the invention may further comprise an amount of an amino acid base sufficient to decrease aggregate formation by the polypeptide or protein during storage of the composition.

By "amino acid base" is intended an amino acid or a combination of amino acids, where any given amino acid is present either in its free base form or in its salt form. The amino acids may be arginine, lysine, aspartic acid, and glutamic acid, aminoguanidine, ornithine and N-monoethyl L-arginine, ethionine and buthionine and S-methyl-L cysteine.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a surfactant. Typical surfactants (with examples of trade names given in brackets [ ]) are polyoxyethylene sorbitan fatty acid esters such as polyoxyethylene (20) sorbitan monolaurate [Tween 20], polyoxyethylene (20) sorbitan monopalmitate [Tween 40] or polyoxyethylene (20) sorbitan monooleate [Tween 80], poloxamers such as polyoxypropylene-polyoxyethylene block copolymer [Pluronic F68/poloxamer 188], polyethylene glycol octylphenyl ether [Triton X-100] or polyoxyethyleneglycol dodecyl ether [Brij 35]. The use of a surfactant in pharmaceutical compositions is well-known to the skilled person. For convenience reference is made to Remington: The Science and Practice of Pharmacy, 19th edition, 1995.

In a further embodiment of the invention the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases or an activated enzyme such as FVIIa in order to inhibit autocatalysis.

Formulations of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to polymers, for example cellulose and derivatives, polysaccharides, for example dextran and derivatives, starch and derivatives, poly(vinyl alcohol), acrylate and methacrylate polymers, polylactic and polyglycolic acid and block copolymers thereof, polyethylene glycols, carrier proteins for example albumin, gels for example, thermogelling systems, for example block co-polymeric systems well known to those skilled in the art, micelles, liposomes, microparticles, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the [compound in the form of a nasal or pulmonal spray. As a still further option, the pharmaceutical compositions containing the [the protein] compound of the invention can also be adapted to transdermal administration, e.g. by needle-free injection or from a patch, optionally an iontophoretic patch, or transmucosal, e.g. buccal, administration. Pharmaceutical formulations for oral application of therapeutic proteins and polypeptides can include encapsulation of the active compound into nanoparticles, microparticles or other kinds of multiparticulate dosage forms. A further option is the use of permeation enhancers such as surface active compounds, cell penetrating peptides, mucoadhesive drug delivery systems, chelating agents and others. A still further option can be the addition of protease inhibitors. Another option is the use of lipid based drug delivery systems such as SEDDS, SMEDDS SNEDDS (Self Emulsifying, Self Micro-Emulsifying or Self Nano-Emulsifying drug delivery systems). Above mentioned drug delivery systems can be formulated into a tablet or filled into a suitable hard or soft capsule which can be coated to release the active compound in a controlled manner or at a preferred intestinal segment.

Potency

The term "potency" as used herein means the measure of the biological activity using a suitably quantitative biological assay (also called potency assay or bioassay), based on the attribute of the product which is linked to the relevant biological properties.

According to the US code of federal regulations, "potency" is defined as the specific ability or capacity of a product, to affect a given result.

Relative Potency (DP/DS)

The term "biological activity" or "activity" or "Relative Potency" (DP/DS) as used herein means a term used in bioassay to refer to the ability of the test sample (drug substance) of unknown potency to produce the desired response compared to the drug product (reference), when tested under the same conditions. Potency of Drug product and Drug substance should not deviate more than 30% and preferably the deviation should be less than 20%.

Particular Embodiments

The invention is further described by the following non-limiting embodiments of the invention:

1. A method for measuring the potency of a drug product relative to a drug substance, wherein the method comprises the steps of:
    (i) contacting cells overexpressing the insulin receptor with said drug product or said drug substance; and
    (ii) Quantifying phosphorylated Akt
    wherein the drug product is an insulin peptide in an oral formulation or is a low affinity insulin peptide in a liquid formulation.

2. The method according to embodiment 1, comprising the step of (ii) quantifying phosphorylated Akt with ELISA.

3. The method according to embodiment 1, comprising the steps of:
    (i) Seeding of cells overexpressing the insulin receptor;
    (ii) Adding/contacting the cells with said drug product or said drug substance;
    (iii) lysing cells;
    (iv) Transferring lysate into ELISA plate pre-coated with rabbit anti-pAkt antibody;
    (v) Quantifying bound pAkt by mouse anti-pAkt antibody;
    (vi) Detecting mouse anti-pAkt antibody by HRP-anti-mouse IgG;
    (vii) Adding substrate for HRP; and
    (viii) Measuring colour development.

4. The method according to embodiments 1 or 3, wherein the cells are Chinese Hamster Ovary cells.

5. The method according to embodiment 3, wherein after step (i) cells are incubated overnight.

6. The method according to embodiment 5, wherein cells are incubated overnight at 37° C.

7. The method according to embodiment 3, wherein in step (ii) cells are contacted with drug product or drug substance at doses in range of 2 nM-20,000 nM.

8. The method according to embodiment 1 or 3, wherein cells are contacted with drug product or drug substance for 10 minutes.

9. The method according to embodiment 3, wherein in step (iii) cells are lysed for 30 minutes.

10. The method according to embodiment 3, wherein in step (iv) rabbit anti-pAkt antibody is Phospho-Akt (Ser473) (193H12) Rabbit mAb.

11. The method according to embodiment 3, wherein in step (v) mouse anti-pAkt antibody is Akt1 isoform specific (2H10) Mouse mAb.

12. The method according to embodiment 3, wherein in step (vi) is a HRP-anti-mouse IgG.

13. The method according to embodiment 3, wherein in step (vii) substrate for HRP is 3,3',5,5'-Tetramethylbenzidine (TMB).

14. The method according to embodiment 3, wherein in step (viii) colour development is measured at 450 nm.

15. The method according to embodiment 1, wherein Akt or protein kinase b (PKB) is selected from a group consisting of isoforms Akt1, Akt2 and Akt3.

16. The method according to embodiment 15, wherein Akt is Akt1.

17. The method according to embodiment 15, wherein Akt is Akt2.

18. The method according to embodiment 15, wherein Akt is Akt3.

19. The method according to embodiment 1, wherein insulin peptide is an insulin analogue or insulin derivative.

20. The method according to embodiment 1, wherein potency of the drug product to the drug substance should not deviate more than 30% and preferably be less than 20%.

21. The method according to embodiment 1, wherein insulin peptide is an insulin analogue or insulin derivative in an oral formulation.

22. The method according to embodiment 21, wherein insulin peptide is an insulin analogue or insulin derivative in an oral formulation further comprising pharmaceutically acceptable excipients.

23. The method according to embodiment 21, wherein insulin derivative is selected from a group consisting of:
    A14E, B25H, desB27, B29K($N^\varepsilon$Octadecanedioyl-γGlu-OEG-OEG), desB30 human insulin;
    A14E, B16H, B25H, 29K($N^\varepsilon$Eicosanedioyl-γGlu), desB30 human insulin;
    A14E, B25H, B29K($N^\varepsilon$Octadecanedioyl-gGlu-OEG-OEG), desB30 human insulin; and
    A14E, B25H, desB27, B29K($N^\varepsilon$-(octadecandioyl-gGlu), desB30 human insulin.

24. The method according to embodiment 23, wherein insulin derivative is A14E, B25H, desB27, B29K ($N^\varepsilon$Octadecanedioyl-γGlu-OEG-OEG), desB30 human insulin.

25. The method according to embodiment 23, wherein insulin derivative is A14E, B16H, B25H, B29K ($N^\varepsilon$Eicosanedioyl-γGlu), desB30 human insulin.

26. The method according to embodiment 23, wherein insulin derivative is A14E, B25H, B29K(N$^\varepsilon$Octadecanedioyl-gGlu-OEG-OEG), desB30 human insulin.

27. The method according to embodiment 23, wherein insulin derivative is A14E, B25H, desB27, B29K (N$^\varepsilon$octadecandioyl-gGlu), desB30 human insulin.

28. The method according to embodiment 22, wherein pharmaceutically acceptable excipients are selected from a group consisting of preservatives, tonicity agents, chelating agents, stabilizers and surfactants.

29. The method according to embodiment 21, wherein insulin analogue or insulin derivative is formulated into tablets.

30. The method according to embodiment 29, wherein tablets are solubilized in a buffer.

31. The method according to embodiment 30, wherein the buffer is PBS or acetonitrile.

32. The method according to embodiment 24, wherein potency of A14E, B25H, desB27, B29K (N$^\varepsilon$Octadecanedioyl-γGlu-OEG-OEG), desB30 human insulin relative to human insulin is 0.0088.

33. The method according to embodiment 26, wherein potency of A14E, B25H, B29K(N$^\varepsilon$Octadecanedioyl-gGlu-OEG-OEG), desB30 human insulin relative to human insulin is 0.0064.

34. The method according to embodiment 1, wherein insulin peptide is an insulin analogue or insulin derivative in a liquid formulation.

35. The method according to embodiment 34, wherein insulin peptide is an insulin analogue or insulin derivative in a liquid formulation comprising pharmaceutically acceptable excipients.

36. The method according to embodiment 1, wherein insulin analogue or insulin derivative has low affinity to insulin receptor relative to human insulin.

37. The method according to embodiment 1, wherein insulin analogues or insulin derivatives have low relative potency i.e. <0.08% of that of Human Insulin when measured according to pAkt assay.

38. The method according to embodiment 34, wherein insulin derivative is selected from a group consisting of A14E, B16E, B25H, B29K(N(eps)eicosanedioyl-gGlu-2×OEG), desB30 human insulin and A14E, B16H, B25H, B29K(N(eps)Eicosanedioyl-γGlu-OEG-OEG), desB30 human insulin.

39. The method according to embodiment 38, wherein insulin derivative is A14E, B16E, B25H, B29K(N(eps) eicosanedioyl-gGlu-2×OEG), desB30 human insulin.

40. The method according to embodiment 38, wherein insulin derivative is A14E, B16H, B25H, B29K(N(eps) Eicosanedioyl-γGlu-OEG-OEG), desB30 human insulin.

41. The method according to embodiment 35, wherein pharmaceutically acceptable excipients are selected from a group consisting of diluents, buffers, preservatives, tonicity agents, isotonic agents, chelating agents, surfactants, protease inhibitors, wetting agents, emulsifiers, antioxidants, bulking agents, metal ions, oily vehicles, proteins and/or a zwitterion and stabilisers.

42. The method according to embodiment 41, wherein excipient is a preservative.

43. The method according to embodiment 42, wherein the excipient is phenol or cresol.

44. The method according to embodiment 39, wherein potency of A14E, B16E, B25H, B29K(N(eps)eicosanedioyl-gGlu-2×OEG), desB30 human insulin is 0.0006 or 0.06% relative to human insulin.

45. The method according to claim 1, wherein potency of a drug product relative to the drug substance is calculated by using $EC_{50}$ values of the drug substance and the drug product.

46. The method according to claim 45, wherein potency of a drug product relative to the drug substance is calculated by $EC_{50}$ drug substance/$EC_{50}$ drug substance.

EXAMPLES

This experimental part starts with a list of abbreviations, and is followed by a section which relates to bioassays. The examples serve to illustrate the invention.

List of Abbreviations
AEBSF: 4-(2-aminoethyl)benzenesulfonyl fluoride hydrochloride
BHK: Baby Hamster Kidney Cell
CHO: Chinese Hamster Ovary
CHO HIR: Chinese Hamster Ovary cells overexpressing Human Insulin Receptor
DPBS: Dulbecco's Phosphate-Buffered Saline
DMEM: Dulbecco's Modified Eagle Medium
DP: Drug Product
DS: Drug Substance
ELISA: Enzyme-linked Immunosorbent Assay
ERK: Extracellular-signal-regulated kinase
FCS: Fetal Calf serum
FOXO: Forkhead box O
HRP: Horseradish Peroxidase
HSA: Human Serum Albumin
pAkt: phosphorylated Akt
PBS: Phosphate-buffered saline
P0, P1, P2:
MEM: Minimum Essential Media
MEM NEAR: Minimum Essential Media Non-Essential Amino Acids
MTX: Methotrexate
RFU: Relative fluorescence units
RT: Room Temperature
SC: Sub-cutaneous
SD: Standard Deviation
SEM: Standard Error of the Mean
TMB: 3,3',5,5'-Tetramethylbenzidine General Methods of Preparation For assay of insulin peptides in oral formulation, tablet (10800 nmol/tb or 800 nmol/tb) was solubilized in 10 ml DPBS (Gibco, cat. no. 14190) with 0.5% FCS in a 15 mL Falcon tube. The tube was turned around for 3 hours at RT on a blood-tube-rotator. The tube was stored at 4° C. overnight. The suspension, without pellet, was transferred to a new tube and subsequently assayed.

A. Insulin Receptor (InsR) Phosphorylation Assay

Cell Line and Cultivation

CHO cells were stably transfected with a vector containing the DNA coding for the human insulin receptor (HIR, +exon 11). The subsequent monoclonal cell line selected was CHO-hIR-A. The cells were maintained in DMEM with glutaMax, 4.5 g/L D-glucose, Na-pyruvate, 10% FBS, 0.9% Minimum Essential Media (MEM), and 0.004 mg/ml MTX in culture flasks in a humidified 5% $CO_2$ incubator and were routinely subcultured every two or three days. The cells were used for assay between passages 13-45, Chemicals and Reagents Media, FBS and chemicals for cultivation of CHO cells were purchased from GIBCO, Ant-HR antibody (Mab IR83-14) was made in-house. Europium labelled anti-PY20 antibody (DELFIA Eu-N1 Anti-Phosphotyrosine (PY20)) was purchased from PerkinElmer®. DELFIA® Assay Buffer, DELFIA® Enhancement Solution, and DELFIA® Wash Concentrate was purchased from PerkinElmer®.

Procedure.

CHO HIR cells were trypsinized using TrypLE™ Select reagent and diluted in assay medium (DMEM with glutamax, 4.5 g/L D-glucose, Na-pyruvate, 9% FBS, and 0.9% MEM), counted and seeded in a flat bottomed 96-well tissue culture plates and incubated overnight at 37° C. and 5% $CO_2$. Meanwhile 96-well polystyrene plates were coated over night at +4 to +8° C. with Mab IR83-14 (PBS, 3 µg/ml Mab83-14). Coating buffer was removed and cold Sabuf buffer (49.5 mM TRIS, 150.6 mM NaCl, 329.4 mM Sorbitol, 0.46% BSA, and 0.05% Sodium azide) was added for at least 2 hours on a shaker (~300 rpm). The CHO HIR cells were washed in PBS and stimulated for 20-30 minutes at 37° C. with increasing amounts of insulin in KREBS incubation buffer (0.11 M NaCl, 4.74 mM KCl, 1.2 mM $KH_2PO_4$, 1.2 mM $MgSO_4$, 5.6% Weltmann's reagent, Tween 20) containing BSA dependent on the insulin type, followed by lysing of the cells for 2 hours at RT on a shaker (~400 rpm) in lysis buffer (150.2 mM NaCl, 50 mM Hepes, 1% Triton-X100, 0.2 M Na-Orthovanadate, 3000 KIU/ml Aprotinin and 100 mM AEBSF). An appropriate amount of cell lysate were transferred to the Mab IR83-12 coated plates and incubated for 1 hour on a shaker (~300 rpm) followed by three washes using DELFIA® Wash. Labelled anti-PY20 diluted to 0.3 µg/ml in DELFIA® Assay Buffer was added and the plates were incubated overnight at (+2 to +8° C.). The plates were washed three times using DELFIA® Wash followed by addition of DELFIA® Enhancement Solution, and incubation for minimum 1 hour on a shaker (~300 rpm). The detection results were collected using a Synergy2 Multi-Mode Reader (Biotek®) in time-resolved mode.

Example 1

InsR Phosphorylation Assay for A14E, B25H, B29K($N^\varepsilon$Octadecanedioyl-gGlu-OEG-OEG), desB30 Human Insulin in Oral Formulation The CHO cell line was transfected to overexpress the human insulin receptor. Cells were stimulated with either DP (A14E, B25H, B29K($N^\varepsilon$Octadecanedioyl-gGlu-OEG-OEG desB30 human insulin) formulated in tablets solubilized in acetonitrile containing buffer at 2700 nmol/tablet) or DS (A14E, B25H, B29K($N^\varepsilon$Octadecanedioyl-gGlu-OEG-OEG desB30 human insulin) for 2 minutes and lysed. An ELISA was used to quantify the phosphorylated insulin receptor. As seen in FIG. 1, each data point represents the mean of triplicates with the standard deviation. The data shows interference from tablet components at the top of the highest concentrations tested well before the max plateau is reached, and therefore the curves cannot be fitted and the potency cannot be calculated. Hence, this assay does not qualify for testing insulin peptide formulated in tablets.

Example 2

Figure 2:
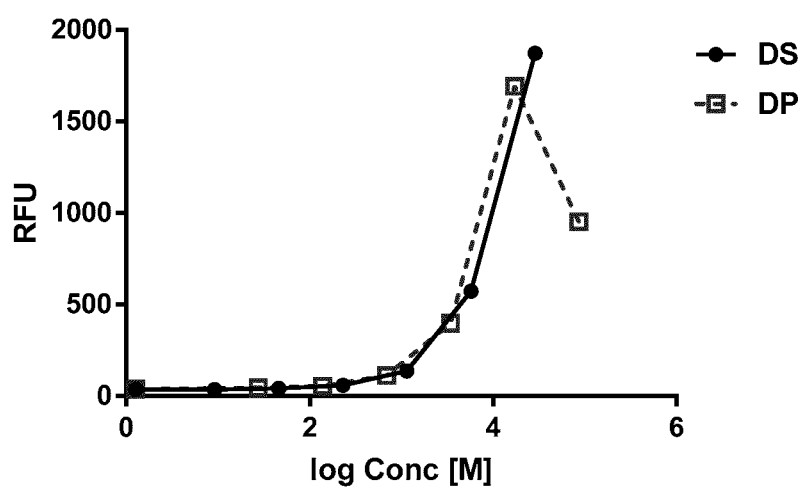
FIG. 2: InsR phosphorylation assay for A14E, B16E, B25H, B29K(N(eps)eicosanedioyl-gGlu-2×OEG), desB30 human insulin (low affinity insulin) in liquid formulation.

InsR Phosphorylation Assay for Low Affinity Insulin A14E, B16E, B25H, B29K(N(Eps)Eicosanedioyl-gGlu-2×OEG), desB30 Human Insulin in Liquid Formulation The CHO cell line was transfected to overexpress the human insulin receptor. Cells were stimulated with either DP (A14E, B16E, B25H, B29K(N(eps)eicosanedioyl-gGlu-2×OEG desB30 human insulin in liquid formulation) or DS (A14E, B16E, B25H, B29K(N(eps)eicosanedioyl-gGlu-2× OEG desB30 human insulin) for 2 minutes and lysed. An ELISA was used to quantify the phosphorylated insulin receptor. As seen in FIG. 2, there is interference from phenol/cresol at the top of the curve well before the max plateau is reached. Hence, this assay does not qualify for testing low affinity insulin peptide in liquid formulation.

B. Reporter Gene Assay

Cell Line and Cultivation

The Syrian hamster cell line, BHK-21 [C-13] (ATCC® CCL-10™), was transfected with three plasmids using the FuGene transfection agent (Promega, cat. no. E2691) according to manufacturer's manual. The three plasmids encode the insulin receptor, GAL4-ELK1 fusion protein and Firefly Luciferase gene under regulation of Upstream Activator Sequence (UAS), respectively. Selection agents (200 µg/ml Hygromycin, 400 µg/ml Zeocin and 600 µg/ml G418) were used to generate a stable cell pool. Single cell clones were isolated by limited dilution and the best performing clone was chosen (clone 26). The subsequent monoclonal cell line selected was maintained in DMEM with glutaMax, 10% Fetal Bovine Serum (FBS), 1% P/S and the above stated selection agents in culture flasks in a humidified 5% $CO_2$ incubator and were routinely sub cultured every two or three days.

Chemicals and Reagents

Media, FBS and chemicals for cultivation of cells were purchased from GIBCO.

Procedure

The cells were released from cell culture flask with 5 ml versene. 50.000 cells were seeded in 150 ul per well in assay medium [DMEM, Glutamin, 0.5% FBS] in white 96w culture plates (Perkin Elmer, cat. no. TC96 6005680). Plates were incubated overnight in 5% $CO_2$ incubator at 37° C. The plates were emptied and 100 µl of relevant samples was added to stimulate the cells. Plates were incubated for 5 hours in 5% $CO_2$ incubator at 37° C. The plates were removed from the incubator and allowed to stand at room temperature for 15 minutes. 100 µl/w aliquot of Steady Glo (Promega, cat. no. E2550) was added. The plates were sealed with TopSeal film (PerkinElmer, cat. no. 6050195). The plates were covered with aluminium foil to protect it from light and were shaken for 15 minutes at room temperature. The plates were analysed on the Envision reader.

Example 3

Figure 3:
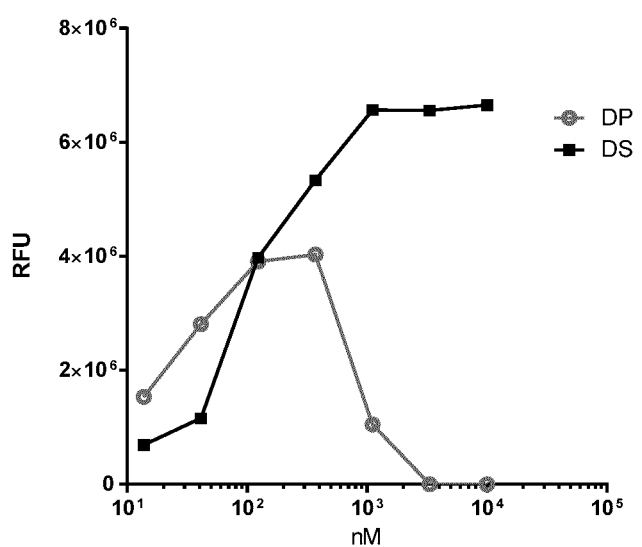
FIG. 3: Reporter Gene Assay for A14E, B25H, desB27, B29K($N^\epsilon$OctadecanedioylγGlu-OEG-OEG), desB30 human insulin in oral formulation.

Reporter Gene Assay for A14E, B25H, desB27, B29K($N^\varepsilon$Octadecanedioyl-γGlu-OEG-OEG), Desb30 Human Insulin in Oral Formulation The BHK cell line was transfected to overexpress the human insulin receptor. The cell line contains a UAS (upstream activating sequence) luciferase plasmid and a plasmid ensuring overexpression of GAL4-ELK1. Cells were stimulated for 4 h with either DP (A14E, B25H, desB27, B29K($N^\varepsilon$OctadecanedioylγGlu-OEG-OEG desB30 human insulin in tablets at 10800 nmol/tablet) or DS (A14E, B25H, desB27, B29K($N^\varepsilon$Octadecanedioyl-γGlu-OEG-OEG desB30 human insulin). As seen in FIG. 3, there is interference from tablet components at the top of the highest concentrations tested well before the max plateau is reached, and therefore the curves cannot be fitted and the potency cannot be calculated. Hence, this assay does not qualify for testing insulin peptide formulated in tablets.

C. pAkt Assay

Insulin peptide (analogues and derivatives) bind to the insulin receptor with a dose dependent effect. Below a certain concentration the response will be too low to measure (minimum asymptote), at higher concentrations the response increases, and at sufficiently high concentrations the response will not increase further (maximum asymptote). The dose-response curve is typically fitted with the Four Parameters Logistic Regression (4PL nonlinear regression model). It is characterized by the sigmoidal shape that fits the bottom and top plateaus of the curve, the $EC_{50}$, and the slope factor (Hill's slope). This curve is symmetrical around its inflection point. The 4PL equation is: $F(x)=D+(A-D)/(1+(x/C)^B)$ where: A=Minimum asymptote. B=Hill's slope (steepness of the curve). C=Inflection point (the point on the curve where the curvature changes direction or signs, also known as $EC_{50}$ corresponding to 50% of maximum response). D=Maximum asymptote (Emax is the maximum possible effect for the agonist).

The term "potency" refers to the $E_{50}$ value. The lower the $EC_{50}$, the less the concentration of a drug is required to produce 50% of maximum effect and the higher the potency.

Assessment of the sensitivity ($EC_{50}$ values) of numerous cellular responses downstream of the insulin receptor in CHO cells over expressing the human insulin receptor, H4IIE cell lines and primary rat adipocytes. For signalling, cells were treated with vehicle or increasing doses of insulin for 30 minutes. Cells were lysed in appropriate buffers and phosphorylation of the insulin receptor, Erk, Akt or Foxo was determined by Western blotting or ELISA, as specified. For mitogenicity, H4IIE cells were incubated with vehicle or increased doses of insulin and cellular growth was measured by detection of thymidine incorporation. For rat free fat cell lipogenesis, primary adipocytes, isolated from collagenase treated epididymal fat pats, were incubated with $H^3$ labelled glucose, vehicle or increasing doses of human insulin. Uptake and conversion of glucose into lipids were measured after 2 hours by extracting lipids into Microscint-e and measuring radioactivity using a top counter.

For all methods: to determine $EC_{50}$ values, data were fitted to a nonlinear 4 parameter regression curve using Graphpad Prism software.

| Assay name | Approximate $EC_{50}$ values (in nM) | Cell type | Method |
|---|---|---|---|
| InsR Phosphorylation | 2 | CHO cells overexpression-human InsR | ELISA |
| ERK phosphorylation | 0.49 | CHO cells overexpression-human InsR | Western blotting |
| Akt phosphorylation | 0.2 | CHO cells overexpression-human InsR | ELISA |
| ERK phosphorylation | 2.3 | H4IIE cells | Western blotting |
| Akt phosphorylation | 0.2 | H4IIE cells | Western blotting |
| FOXO phosphorylation | 0.02 | H4IIE cells | Western blotting |
| Mitogenecity (thymidine incorporation) | 1 | H4IIE cells | Require radioactively labelled thymidine |
| Rat Free Fat Cell lipogenesis | 0.02 | Isolated primary rat adipocytes | Require animals and radioactive labelled glucose |

Akt was found to be a sensitive read out. Other sensitive read outs such as FOXO could not be used because it is very difficult to raise antibodies for use in FOXO phosphorylation assay.

Cell Line and Cultivation

CHO cells were stably transfected with a vector containing the DNA coding for the human insulin receptor (HIR, +exon 11). The subsequent monoclonal cell line selected was CHO-hIR-A. The cells were maintained in DMEM with glutaMax, 4.5 g/L D-glucose, Na-pyruvate, 10% FBS, 0.9% Minimum Essential Media (MEM), and 0.004 mg/ml MTX in culture flasks in a humidified 5% $CO_2$ incubator and were routinely sub cultured every two or three days. The cells were used for assay between passages 13-45.

Chemicals and Reagents

Media, FBS and chemicals for cultivation of PTH CHO cells were purchased from GIBCO. Antibodies and TMB were purchased from Cell Signaling Technology®.

Procedure

10000 FCW128-5 cells per well were seeded in flat bottom 96w plates (Nunc) in 100 uL DMEM medium described above. Plates were incubated overnight, 37° C., 5% $CO_2$. Medium was exchanged with 80 μl/w starvation medium: DMEM with 0.5% HSA (Sigma), 1% P/S, 1% MEM NEAA, 4 μg/ml MTX, and incubated 5 h, 37 C, 5% CO2. Cells were subsequently stimulated with 20 μl per well of relevant sample at 5× final concentration per well in starvation medium for 10 min at 37° C., 5% $CO_2$. Plates were places on ice, emptied and washed with 100 μl cold PBS per well and again emptied. 20 μl cold lysis buffer [(Biosource cell extracting buffer (Life Technologies), 1 mM AEBSF (Life Technologies), protease inhibitor cocktail (Sigma)] was added per well. Plates were incubated on ice for 30 min (mix three times). Lysates were transferred to pre-coated ELISA plates for content measurement of pAkt (see below).

96w half-area ELISA plates (Costar) were coated with 50 μl per well 0.5 μg/ml anti-phospho-Akt rabbit mAb, clone 193H12, (Cell Signalling) in DPBS (Gibco) and incubated at 4° C. overnight. The ELISA plates were washed four times with 125 μl/well washing buffer (DPBS 0.05% tween20). 125 μl/well blocking buffer (DPBS, 0.05% tween20, 1% BSA) was added and plates were incubated for 2 h at room temp. The ELISA plates were washed four times. 50 μl/well cell lysis was added and the plates were incubated overnight, shaking at room temp. The ELISA plates were washed four times. 50 μl of 0.7 μg/ml anti-phospho-Akt mouse mAb, clone 2H10, (Cell Signalling) in blocking buffer was added per well. Plates were incubated 1 h at room temp. The ELISA plates were washed four times. 50 μl 1:1000 diluted Anti mouse IgG, HRP-linked antibody (Cell Signalling) was added per well. Plates were incubated 30 min at room temp. The ELISA plates were washed four times. 50 μl TMB (Kem-En-Tec) was added per well. The reaction was stopped after app. 8 min. by 50 μl 4M Phosphoric acid per well. The colour development was quantified by an ENVISION reader (Perkin Elmer) at 450 nm. Analytical results are influenced by "biological variance" (e.g. an intermediary precision of assay results of upto around 15% for an assay is considered to be normal).

Figure 4:
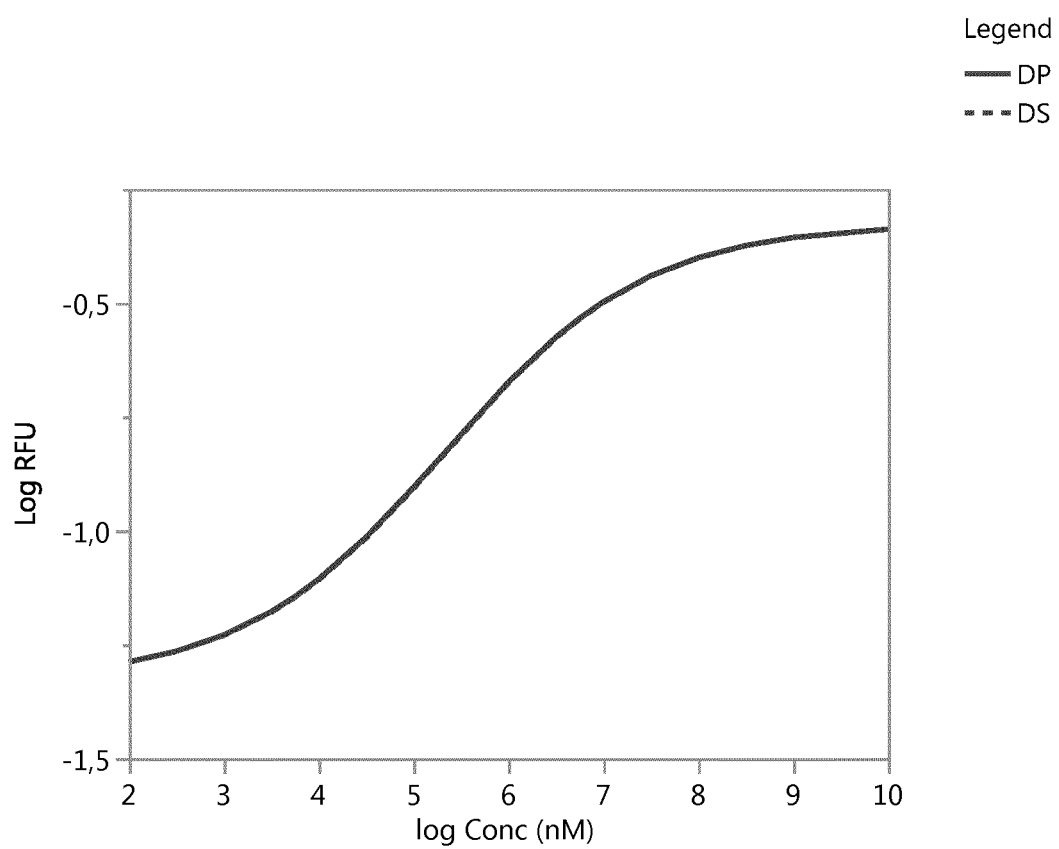
FIG. 4: pAkt assay for A14E, B16E, B25H, B29K(N(eps)eicosanedioyl-gGlu-2×OEG), desB30 human insulin (low affinity insulin) in liquid formulation.

Example 4 pAkt Assay for Low Insulin A14E, B16E, 825H, B29K(N (Eps)Eicosanedioyl-gGlu-2×OEG), desB30 Human Insulin in Liquid Formulation The CHO cell line was transfected to overexpress the human insulin receptor. Cells were stimulated with either DP (A14E, B16E, B25H, B29K(N(eps)eicosanedioyl-gGlu-2×OEG desB30 human insulin formulated in 25 mM phenol and 25 mM m-cresol at 4200 nmol/ml for SC delivery) or DS (A14E, B16E, B25H, B29K(N(eps)eicosanedioyl-gGlu-2×OEG desB30 human insulin) for 10 minutes and lysed. An ELISA was used to quantify the phosphorylated Akt1. As seen in FIG. 4, data points represent mean of triplicates +/−SD. Therefore, in the bioassay, there is no interference from excipients phenol/cresol.

The relative potency obtained are shown in the below table. The potency of the DP deviates from the DS with 2%.

| Insulin | Relative Potency | $EC_{50}$ (nM) |
|---|---|---|
| DS | 1 | 619 |
| DP | 1.02 | 591 |

Figure 5A:
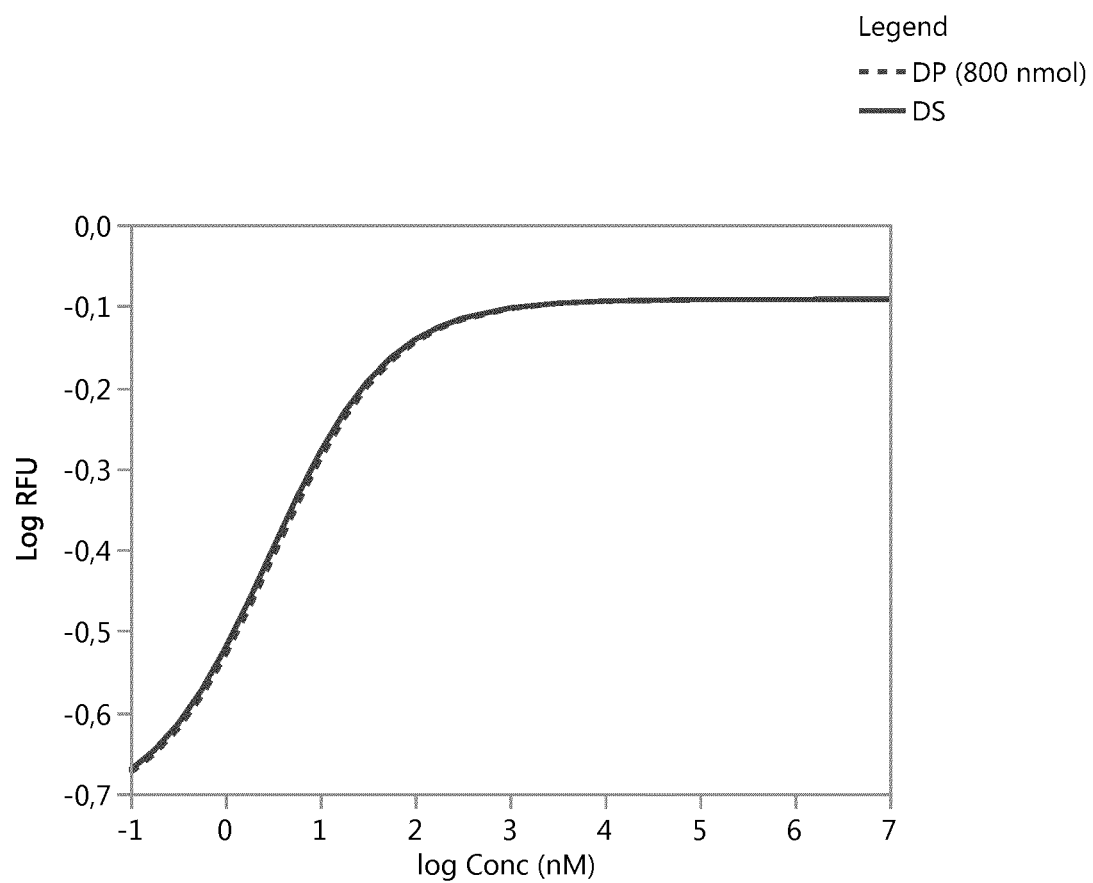
FIG. 5: pAkt assay for A14E, B25H, desB27, B29K($N^\epsilon$Octadecanedioyl-γGlu-OEG-OEG), desB30 human insulin in oral formulation.
Figure 5B:
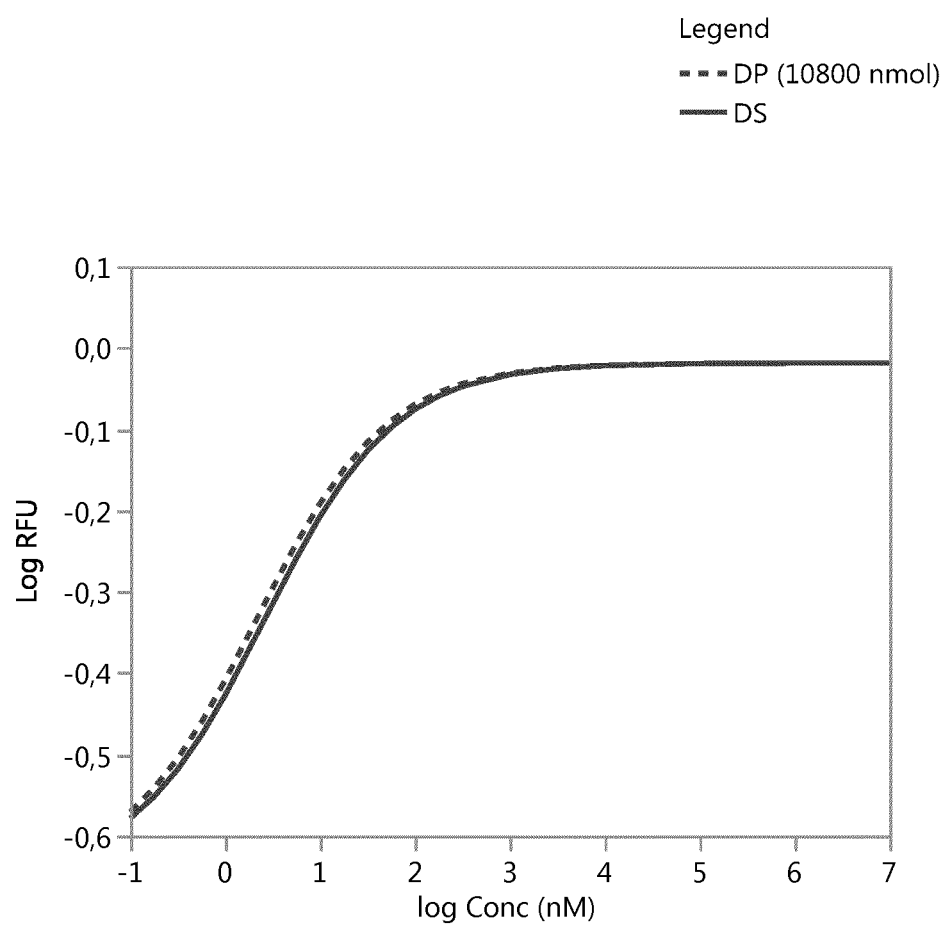

Example 5 pAkt Assay for A14E, B25H, desB27, B29K(N$^\varepsilon$Octadecanedioyl-γGlu-OEG-OEG), desB30 Human Insulin in Oral Formulation The CHO cell line was transfected to overexpress the human insulin receptor. Cells were stimulated with either DP (A14E, B25H, desB27, B29K(N$^\varepsilon$Octadecanedioyl-γGly-OEG-OEG desB30 human insulin in tablet solubilized in acetonitril containing buffer) or DS (A14E, B25H, desB27, B29K(N$^\varepsilon$Octadecanedioyl-gGlu-OEG-OEG) desB30 human insulin) for 10 min. and lysed. An ELISA was used to quantify the phosphorylated Akt1. As seen in FIG. 5a, data points represent mean of triplicates +/−SD. FIG. 5 a) represents low dose tablets (800 nmol/tablet). There is no interference from tablet excipients.

The relative potency obtained are shown in the below table. The potency of the DP (800 nmol tablets) deviates from the DS with 9%.

| Insulin | Relative Potency | $EC_{50}$ (nM) |
|---|---|---|
| DS | 1 | 25 |
| DP (800 nmol) | 0.91 | 25 | and FIG. 5 b) represents high dose tablets (10800 nmol/tablet). There is no interference from tablet excipients.

The relative potency obtained are shown in the below table. The potency of the DP (10800 nmol tablets) deviates from the DS with 22%.

| Insulin | Relative Potency | $EC_{50}$ (nM) |
|---|---|---|
| DS | 1 | 25 |
| DP (10800 nmol) | 1.22 | 24 |

Figure 6:
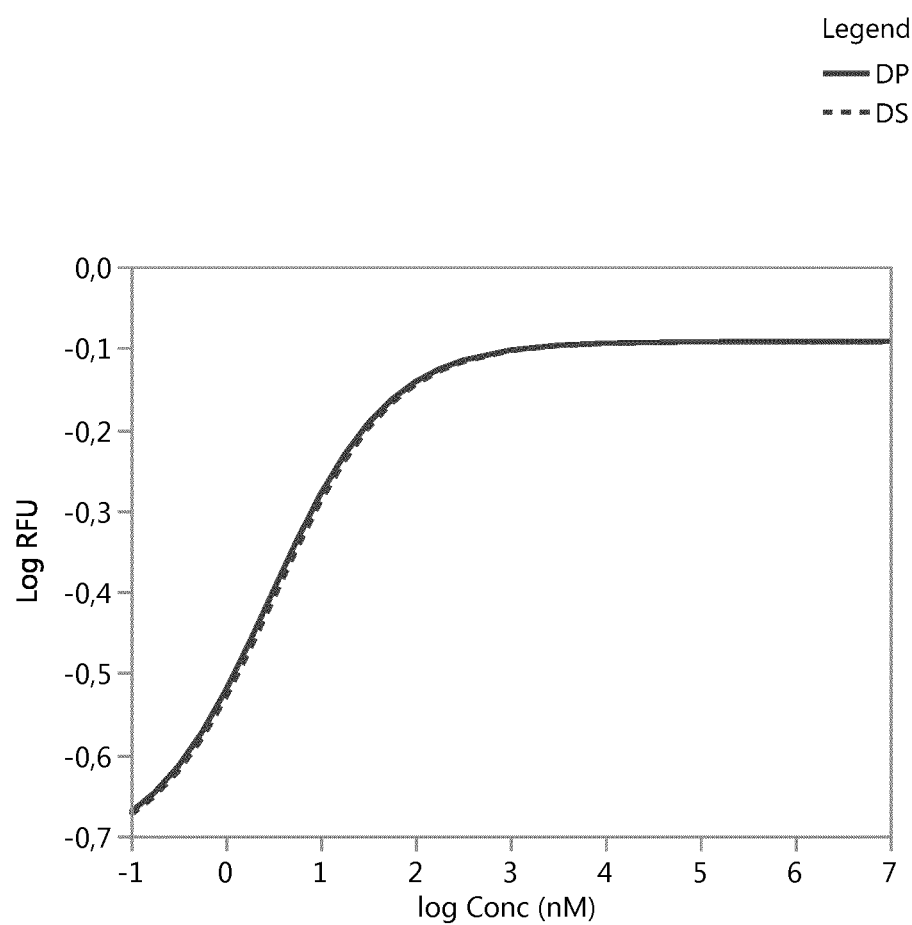
FIG. 6: pAkt assay for A14E, B25H, B29K($N^\epsilon$Octadecanedioyl-gGlu-OEG-OEG), desB30 human insulin in oral formulation.

Example 6 pAkt Assay for A74E, B25H, B29K(N$^\varepsilon$Octadecanedioyl-gGlu-OEG-OEG), desB30 Human Insulin in Oral Formulation The CHO cell line was transfected to overexpress the human insulin receptor. Cells were stimulated with either DP (A14E, B25H, B29K(N$^\varepsilon$Octadecanedioyl-gGlu-OEG-OEG desB30 human insulin in 2700 nmol/tablet solubilized in acetonitril containing buffer) or DS (A14E, B25H, B29K(N$^\varepsilon$Octadecanedioyl-gGlu-OEG-OEG desB30 human insulin) for 10 minutes and lysed. An ELISA was used to quantify the phosphorylated Akt1. As seen in FIG. 6, data points represent mean of triplicates +/−SD. Therefore, in the bioassay, there is no interference from tablet components. The relative potency obtained are shown in the below table. The potency of the DP deviates from the DS with 3% which means that the relative potency (DP/DS) is preferable.

| Insulin | Relative Potency | $EC_{50}$ (nM) |
|---|---|---|
| DS | 1 | 44 |
| DP | 0.97 | 47 |

Figure 7:
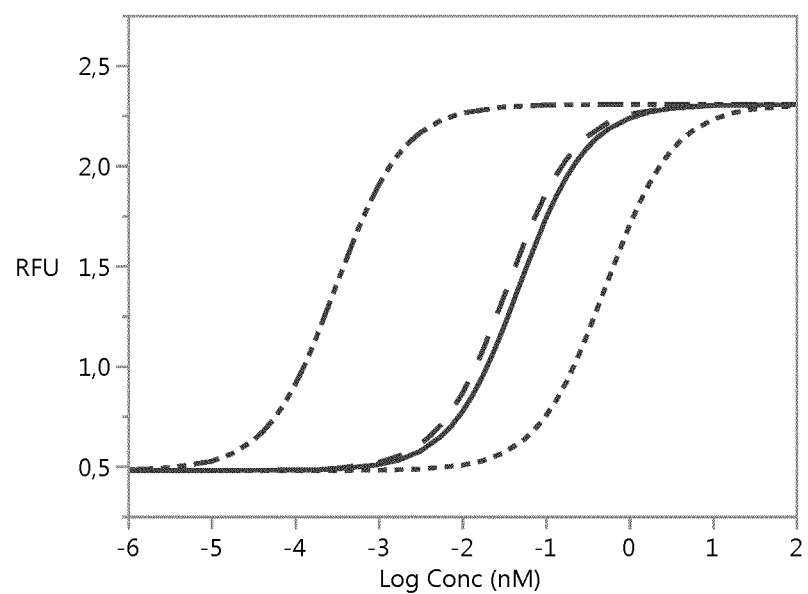
FIG. 7: Potencies of (i) A14E, B16E, B25H, B29K(N(eps)eicosanedioyl-gGlu-2×OEG), desB30 human insulin; (ii) A14E, B25H, desB27, B29K($N^\epsilon$Octadecanedioyl-γGlu-OEG-OEG), desB30 human insulin; (iii) A14E, B25H, B29K($N^\epsilon$Octadecanedioyl-gGlu-OEG-OEG), desB30 human insulin; and human insulin in pAkt assay.

Comparative Example 7 pAkt Assay for (i) A14E, B16E, B25H, B29K(N(Eps)Eicosanedioyl-gGlu-2×OEG), desB30 Human Insulin; (ii) A14E, B25H, desB27, B29K(N$^\varepsilon$Octadecanedioyl-γGlu-OEG-OEG), desB30 Human Insulin; (iii) A14E, B25H, B29K(N$^\varepsilon$Octadecanedioyl-gGlu-OEG-OEG), desB30 Human Insulin; and Human Insulin Three human insulin analogues [(i), (ii) and (iii)] were compared to human insulin in an assay used to measuring the potency of insulin analogues by quantifying the level of phosphorylation of Akt. The CHO cell line was transfected to overexpress the human insulin receptor. Cells were stimulated insulin and analogues hereof for 10 minutes and lysed. ELISA was used to quantify the phosphorylated Akt. The potency was calculated using SAS JMP 12.2.0 4 parameter logistic regression (4PL). The relative potency was subsequently calculated as: $EC_{50 Analogue\ or\ derivative}/EC_{50 human\ insulin}$. The analogues rank in the following order: A14E, B16E, B25H, B29K(N(eps)eicosanedioyl-gGlu-2× OEG) desB30 human insulin, A14E, B25H, B29K (N$^\varepsilon$Octadecanedioyl-gGlu-OEG-OEG) desB30 human insulin and A14E, B25H, desB27, B29K(N$^\varepsilon$Octadecanedioyl-γGlu-OEG-OEG) desB30 human insulin, with the latter displaying the highest potency. As seen in FIG. 7, relative to human insulin, analogue A14E, B25H, B29K (N$^\varepsilon$Octadecanedioyl-γGlu-OEG-OEG), desB30 human insulin displays 0.64% relative potency, analogue A14E, B25H, desB27, B29K(N$^\varepsilon$Octadecanedioyl-γGlu-OEG-OEG), desB30 human insulin; displays 0.88% relative potency and analogue A14E, B16E, B25H, B29K(N(eps) eicosanedioyl-gGlu-2×OEG), desB30 human insulin displays 0.06% relative potency. It is evident from this example that A14E, B16E, B25H, B29K(N(eps)eicosanedioyl-gGlu-2×OEG), desB30 human insulin is a low affinity and low potency insulin. The data illustrates the ability of this assay to function over a very broad range in terms of potency of different analogues.

| Insulin | Relative Potency | $EC_{50}$ (nM) |
|---|---|---|
| A14E, B16E, B25H, B29K(N(eps)eicosanedioyl-gGlu-2xOEG), desB30 human insulin | 0.0006 or 0.06% | 522 |
| A14E, B25H, desB27, B29K(N$^\varepsilon$Octadecanedioyl-γGlu-OEG-OEG), desB30 human insulin | 0.0088 or 0.88% | 35 |
| A14E, B25H, B29K(NεOctadecanedioyl-gGlu-OEG-OEG), desB30 human insulin | 0.0064 or 0.64% | 48 |
| Human | 1 or 100% | 0.31 |

Calculation of Potency

The experiments were performed by stimulating the cells with human insulin or analogues hereof at seven different concentrations, making a full titration curve with top and bottom plateau. Each concentration is performed in triplicates.

Potency was calculated using SAS JMP 12.2.0 4 parameter logistic regression (4PL) according to section 4.6 of United States Pharmacopeia and section 5.3 of European Pharmacopoeia 7.0. Potency can also be calculated by using other known softwares in the art. However, analytical results are influenced by "biological variance" (e.g. an intermediary precision of assay results of 15% for an assay is normal)

In a 4PL bioassay, a four-parameter logistic (4PL) function is fitted to the measured assay response as function of the log-concentration of the product under study. The 4PL function has the following parameterisation in JMP, where x is the natural logarithm of the dose:

$$f(x) = c + \frac{d-c}{1 + \exp(-a(x-b))}$$

where
a growth rate
b Inflection point
c Lower asymptote
d Upper asymptote

The inflection point b determines the log-dose where the response attains the value half-way between the lower and upper asymptotes. The corresponding value on the original dose scale is denoted $EC_{50}$ and is given by:

$$EC50 = \exp(b)$$

If the curves are parallel the relative potency of the drug product relative to the drug substance is the ratio of the $EC_{50}$ values, $$RP = \frac{EC50_{Drug\ Substance}}{EC50_{Drug\ Product}}$$

When relative potency is discussed as percentage the above number is multiplied with 100%.

Potency of Drug product and Drug substance should not deviate more than 30% and preferably the deviation should be less than 20%.

The invention claimed is:

1. A method for measuring the potency of a drug product relative to a drug substance, wherein said drug product comprises said drug substance as its active pharmaceutical ingredient, wherein the method comprises the steps of:
  (i) Contacting cells overexpressing the insulin receptor with said drug product and said drug substance, respectively;
  (ii) Quantifying phosphorylated Akt; and
  (iii) Determining $EC_{50}$ values;
  wherein the potency of the drug product relative to the drug substance is the ratio of the $EC_{50}$ values, and is calculated by the following formula:

relative potency=$EC_{50}$(drug substance)/$EC_{50}$(drug product); and wherein the drug product is an insulin peptide in an oral formulation or is a low affinity insulin peptide in a liquid formulation, wherein Akt is selected from the group consisting of isoforms Akt1, Akt2 and Akt3, and wherein the drug product comprises a pharmaceutically acceptable excipient selected from the group consisting of a preservative, a tonicity agent, a chelating agent, a stabilizer and a surfactant.

2. The method according to claim 1, wherein Akt is Akt1.

3. The method according to claim 1, wherein the insulin peptide is an insulin analogue or insulin derivative.

4. The method according to claim 3, wherein the drug product is an insulin analogue or insulin derivative in an oral formulation.

5. The method according to claim 1, wherein the drug product is an insulin analogue or insulin derivative in an oral formulation.

6. The method according to claim 5, wherein the insulin analogue or insulin derivative is selected from the group consisting of:
  A14E, B25H, desB27, B29K($N^\varepsilon$Octadecanedioyl-γGlu-OEG-OEG), desB30 human insulin;
  A14E, B16H, B25H, 29K($N^\varepsilon$Eicosanedioyl-γGlu), desB30 human insulin;
  A14E, B25H, B29K($N^\varepsilon$Octadecanedioyl-gGlu-OEG-OEG), desB30 human insulin; and
  A14E, B25H, desB27, B29K($N^\varepsilon$-(octadecandioyl-gGlu), desB30 human insulin.

7. The method according to claim 5, wherein the excipient is a preservative.

8. The method according to claim 3, wherein insulin analogue or insulin derivative is formulated into tablets.

9. The method according to claim 3, wherein the drug product is an insulin analogue or insulin derivative in a liquid formulation.

10. The method according to claim 9, wherein the insulin analogue or insulin derivative has low affinity to insulin receptor relative to human insulin.

11. The method according to claim 9, wherein the insulin analogue or insulin derivative is selected from the group consisting of A14E, B16E, B25H, B29K(N(eps)eicosanedioyl-gGlu-2×OEG), desB30 human insulin and A14E, B16H, B25H, B29K(N(eps)Eicosanedioyl-γGlu-OEG-OEG), desB30 human insulin.

* * * * *

SEQUENCE LISTING

```
<160> NUMBER OF SEQ ID NOS: 12

<210> SEQ ID NO 1
<211> LENGTH: 21
<212> TYPE: PRT
<213> ORGANISM: Artificial Sequence
<220> FEATURE:
<223> OTHER INFORMATION: Modified Insulin Chain A
<220> FEATURE:
<221> NAME/KEY: MISC_FEATURE
<222> LOCATION: (14)..(14)
<223> OTHER INFORMATION: The amino acid in position 14 is glutamic acid
<220> FEATURE:
<221> NAME/KEY: MISC_FEATURE
<222> LOCATION: (14)..(14)
<223> OTHER INFORMATION: Amino acid in this position is glutamic acid

<400> SEQUENCE: 1

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 2
<211> LENGTH: 29
<212> TYPE: PRT
<213> ORGANISM: Artificial Sequence
<220> FEATURE:
<223> OTHER INFORMATION: Modified Insulin Chain B
<220> FEATURE:
<221> NAME/KEY: MISC_FEATURE
<222> LOCATION: (16)..(16)
<223> OTHER INFORMATION: Amino acid in position 16 is glutamic acid
<220> FEATURE:
<221> NAME/KEY: MISC_FEATURE
<222> LOCATION: (25)..(25)
<223> OTHER INFORMATION: Amino acid in position 25 is histidine
<220> FEATURE:
<221> NAME/KEY: MOD_RES
<222> LOCATION: (29)..(29)

<400> SEQUENCE: 2

Phe Val Asn Gln His Leu Cys Gly Ser His Leu Val Glu Ala Leu Glu
```

```
                1               5                  10                 15
Leu Val Cys Gly Glu Arg Gly Phe His Tyr Thr Pro Lys
                20                  25

<210> SEQ ID NO 3
<211> LENGTH: 21
<212> TYPE: PRT
<213> ORGANISM: Artificial Sequence
<220> FEATURE:
<223> OTHER INFORMATION: Modified Insulin Chain A
<220> FEATURE:
<221> NAME/KEY: MISC_FEATURE
<222> LOCATION: (14)..(14)
<223> OTHER INFORMATION: Amino acid in position 14 is glutamic acid

<400> SEQUENCE: 3

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 4
<211> LENGTH: 29
<212> TYPE: PRT
<213> ORGANISM: Artificial Sequence
<220> FEATURE:
<223> OTHER INFORMATION: Modified Insulin Chain B
<220> FEATURE:
<221> NAME/KEY: MISC_FEATURE
<222> LOCATION: (16)..(16)
<223> OTHER INFORMATION: The amino acid in this position is histidine
<220> FEATURE:
<221> NAME/KEY: MISC_FEATURE
<222> LOCATION: (25)..(25)
<223> OTHER INFORMATION: Amino acid in this position is histidine
<220> FEATURE:
<221> NAME/KEY: MOD_RES
<222> LOCATION: (29)..(29)
<220> FEATURE:
<221> NAME/KEY: MOD_RES
<222> LOCATION: (29)..(29)
<223> OTHER INFORMATION: N(eps)Eicosanedioyl-?Glu-OEG-OEG

<400> SEQUENCE: 4

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
                20                  25

<210> SEQ ID NO 5
<211> LENGTH: 21
<212> TYPE: PRT
<213> ORGANISM: Artificial Sequence
<220> FEATURE:
<223> OTHER INFORMATION: Modified Insulin Chain A
<220> FEATURE:
<221> NAME/KEY: MISC_FEATURE
<222> LOCATION: (14)..(14)
<223> OTHER INFORMATION: Amino acid in this position is glutamic acid

<400> SEQUENCE: 5

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 6
<211> LENGTH: 28
```

```
<212> TYPE: PRT
<213> ORGANISM: Artificial Sequence
<220> FEATURE:
<223> OTHER INFORMATION: Modified Insulin Chain B
<220> FEATURE:
<221> NAME/KEY: MISC_FEATURE
<222> LOCATION: (25)..(25)
<223> OTHER INFORMATION: Amino acid in this position is histidine
<220> FEATURE:
<221> NAME/KEY: MISC_FEATURE
<222> LOCATION: (27)..(27)
<223> OTHER INFORMATION: Amino acid in this position is absent
<220> FEATURE:
<221> NAME/KEY: MISC_FEATURE
<222> LOCATION: (27)..(27)
<223> OTHER INFORMATION: Amino acid in this position is absent
<220> FEATURE:
<221> NAME/KEY: MOD_RES
<222> LOCATION: (27)..(27)
<223> OTHER INFORMATION: N(eps)Octadecanedioyl- Glu-OEG-OEG

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe His Tyr Pro Lys
            20                  25

<210> SEQ ID NO 7
<211> LENGTH: 21
<212> TYPE: PRT
<213> ORGANISM: Artificial Sequence
<220> FEATURE:
<223> OTHER INFORMATION: Modified Insulin Chain A
<220> FEATURE:
<221> NAME/KEY: MISC_FEATURE
<222> LOCATION: (14)..(14)
<223> OTHER INFORMATION: Amino acid in this position is glutamic acid

<400> SEQUENCE: 7

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 8
<211> LENGTH: 29
<212> TYPE: PRT
<213> ORGANISM: Artificial Sequence
<220> FEATURE:
<223> OTHER INFORMATION: Modified Insulin Chain B
<220> FEATURE:
<221> NAME/KEY: MISC_FEATURE
<222> LOCATION: (16)..(16)
<223> OTHER INFORMATION: Amino acid in this position is histidine
<220> FEATURE:
<221> NAME/KEY: MISC_FEATURE
<222> LOCATION: (25)..(25)
<223> OTHER INFORMATION: Amino acid in this position is histidine
<220> FEATURE:
<221> NAME/KEY: MOD_RES
<222> LOCATION: (29)..(29)
<220> FEATURE:
<221> NAME/KEY: MOD_RES
<222> LOCATION: (29)..(29)
<223> OTHER INFORMATION: N(eps)Eicosanedioyl-gGlu

<400> SEQUENCE: 8

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25
```

```
<210> SEQ ID NO 9
<211> LENGTH: 21
<212> TYPE: PRT
<213> ORGANISM: Artificial Sequence
<220> FEATURE:
<223> OTHER INFORMATION: Modified Insulin Chain A
<220> FEATURE:
<221> NAME/KEY: MISC_FEATURE
<222> LOCATION: (14)..(14)
<223> OTHER INFORMATION: Amino acid in this position is glutamic acid

<400> SEQUENCE: 9

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 10
<211> LENGTH: 29
<212> TYPE: PRT
<213> ORGANISM: Artificial Sequence
<220> FEATURE:
<223> OTHER INFORMATION: Modified Insulin Chain B
<220> FEATURE:
<221> NAME/KEY: MISC_FEATURE
<222> LOCATION: (25)..(25)
<223> OTHER INFORMATION: Amino acid in this position is histidine
<220> FEATURE:
<221> NAME/KEY: MOD_RES
<222> LOCATION: (29)..(29)
<220> FEATURE:
<221> NAME/KEY: MOD_RES
<222> LOCATION: (29)..(29)
<223> OTHER INFORMATION: N(eps)Octadecanedioyl-gGlu-OEG-OEG

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Lys
            20                  25

<210> SEQ ID NO 11
<211> LENGTH: 21
<212> TYPE: PRT
<213> ORGANISM: Artificial Sequence
<220> FEATURE:
<223> OTHER INFORMATION: Modified Insulin Chain A
<220> FEATURE:
<221> NAME/KEY: MISC_FEATURE
<222> LOCATION: (14)..(14)
<223> OTHER INFORMATION: Amino acid in this position is glutamic acid

<400> SEQUENCE: 11

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 12
<211> LENGTH: 28
<212> TYPE: PRT
<213> ORGANISM: Artificial Sequence
<220> FEATURE:
<223> OTHER INFORMATION: Modified Insulin Chain B
<220> FEATURE:
<221> NAME/KEY: MISC_FEATURE
<222> LOCATION: (25)..(25)
<223> OTHER INFORMATION: Amino acid in this position is histidine
```

```
<220> FEATURE:
<221> NAME/KEY: MISC_FEATURE
<222> LOCATION: (27)..(27)
<223> OTHER INFORMATION: Amino acid in this position is absent
<220> FEATURE:
<221> NAME/KEY: MOD_RES
<222> LOCATION: (28)..(28)
<223> OTHER INFORMATION: N(eps)-(octadecandioyl-gGlu

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe His Tyr Pro Lys
            20                  25
```